United States Patent
Inaba et al.

(10) Patent No.: US 10,444,168 B2
(45) Date of Patent: Oct. 15, 2019

(54) METHOD AND APPARATUS FOR MEASURING BOWING OF SINGLE-CRYSTAL SUBSTRATE

(71) Applicant: Rigaku Corporation, Akishima-shi (JP)

(72) Inventors: Katsuhiko Inaba, Ome (JP); Shintaro Kobayashi, Fussa (JP); Toru Mitsunaga, Hachioji (JP)

(73) Assignee: RIGAKU CORPORATION, Akishima-Shi, Tokyo (JP)

( * ) Notice: Subject to any disclaimer, the term of this patent is extended or adjusted under 35 U.S.C. 154(b) by 1401 days.

(21) Appl. No.: 14/251,829

(22) Filed: Apr. 14, 2014

(65) Prior Publication Data

US 2014/0379282 A1   Dec. 25, 2014

(30) Foreign Application Priority Data

Jun. 24, 2013   (JP) .................. 2013-131410

(51) Int. Cl.
    *G01N 23/20*    (2018.01)

(52) U.S. Cl.
    CPC .................... *G01N 23/20* (2013.01)

(58) Field of Classification Search
    CPC ..................................................... G01N 23/20
    See application file for complete search history.

(56) References Cited

U.S. PATENT DOCUMENTS

2003/0128809 A1*   7/2003   Umezawa ........... G01N 23/20
    378/70

FOREIGN PATENT DOCUMENTS

| JP | 63-279148 A | 11/1988 |
|---|---|---|
| JP | 2010-91354 A | 4/2010 |
| JP | 2010-217127 A | 9/2010 |

OTHER PUBLICATIONS

Doucette et al., "Precise orientation of single crystals by a simple x-ray diffraction rocking curve method", Review of Scientific Instruments 2005 76:3.*

(Continued)

*Primary Examiner* — John E Breene
*Assistant Examiner* — Jeffrey C Morgan
(74) *Attorney, Agent, or Firm* — Buchanan Ingersoll & Rooney PC

(57) ABSTRACT

At least two values of an X-ray irradiation width are set for a single specimen. A rocking curve is measured for each of the X-ray irradiation widths. A rocking curve width value is determined for each of the rocking curves. The values of the X-ray irradiation width and the values of the rocking curve width are plotted on a planar coordinate system having a vertical axis representing the rocking curve width value and a horizontal axis representing the X-ray irradiation width value, and a rocking curve width shift line is determined based on the plotted points. A gradient of the rocking curve width shift line is determined. A curvature radius of the specimen is determined based on the gradient. The amount of bowing of a single-crystal substrate under measurement can be measured without a need to move the single-crystal substrate for reliable measurement with a small amount of error.

1 Claim, 12 Drawing Sheets

(56) References Cited

OTHER PUBLICATIONS

Aida et al., "Estimation of bowing in hetero-epitaxial GaN-on-sapphire substrate at elevated temperatures by X-ray diffraction rocking curve measurement", Journal of Crystal Growth 412 (2015) 60-66.*

Hidehito Asaoka et al., Real-time Stress Measurement in Ge/Si (111)-7×7 Heteroepitaxial Growth, Journal of the Surface Science of Japan, vol. 28, No. 9, 2007, pp. 500-503.

* cited by examiner (WR4 > WR3)

METHOD AND APPARATUS FOR MEASURING BOWING OF SINGLE-CRYSTAL SUBSTRATE

BACKGROUND OF THE INVENTION

Field of the Invention

The present invention relates to a bowing measurement method and apparatus for measuring the amount of bowing of a silicon substrate, a sapphire substrate, and other single-crystal substrates.

Description of the Related Art

In recent years, attention has been directed toward GaN (gallium nitride), AlN (aluminum nitride), SiC (silicon carbide), and other wide-bandgap semiconductor materials. For example, the following semiconductor parts have been receiving attention:

(1) A part used in an LED (light emitting diode) and formed of a single-crystal structure made of GaN deposited on a single-crystal sapphire substrate (GaN/sapphire);

(2) A part used in a power device and formed of a single-crystal structure made of GaN deposited on a single-crystal silicon (Si) substrate (GaN/Si);

(3) A part used in a frequency filler that is an SAW (surface acoustic wave) device and formed of a single-crystal structure made of AlN deposited on a single-crystal Si substrate (AlN/Si); and (4) A part used in a power device and formed of a single-crystal structure made of SiC deposited on an appropriate single-crystal substrate.

A single-crystal structure made of a semiconductor material or any other material deposited on a single-crystal substrate as described above desirably has a precisely flat surface. In practice, however, a crystal growth process or an epitaxial film formation process causes a single-crystal substrate to have bowing in some cases. When the single-crystal substrate has bowing, the bowing may affect device characteristics of a final product and cause a problem in using a process technology for manufacturing a final product (that is, technology for forming a variety of elements on a substrate).

Since whether or not a single-crystal substrate has bowing greatly affects characteristics of a final product manufactured based on the single-crystal substrate, it is very important to evaluate the amount of bowing.

A laser-beam-based method has been known as a method for measuring the amount of bowing of a single-crystal substrate (Non-Patent Citation 1, for example). The method includes irradiating a specimen surface with a plurality of collimated laser beams, measuring the position of each of the laser beams reflected off the specimen surface, and evaluating the amount of bowing of the specimen based on the distribution of the positions. In the conventional laser-beam-based method for measuring the amount of bowing, however, the exterior appearance of a target object is observed, but the amount of bowing of a crystal lattice plane of a single-crystal substrate is not measured.

As a method that allows measurement of the amount of bowing itself of a crystal plane, Patent Citations 1 and 2, for example, disclose conventional X-ray-based measurement methods. The conventional measurement methods include the steps of irradiating a surface of a target object with X-rays in a position under measurement to acquire a rocking curve and determining a peak position of the rocking curve. The methods further include moving the X-rays and the target object relative to each other and carrying out the same steps on one or more positions under measurement to determine a peak position of a rocking curve in each of the positions under measurement. The methods finally include calculating the curvature radius (that is, the amount of bowing) of the single-crystal substrate based on how the peak position of the rocking curve changes when the position under measurement is changed.

FIG. 11A shows an example of the relationship between the bowing and the curvature radius. Specifically, the amount of bowing is the distance C from the line that connects both ends of a measured area A of a single-crystal substrate 101. The horizontal axes of FIGS. 11B and 11C represent the curvature radius R corresponding to the bowing C. In FIGS. 11B and 11C, the vertical axes represent the amount of bowing C, and the horizontal axes represent the curvature radius R.

PRIOR ART CITATION (Patent Citation 1): JP-A 2010-091354
(Patent Citation 2): JP-A 2010-217127
(Non-Patent Citation 1): Journal of the Surface Science of Japan, Vol. 28, No. 9, pp. 500-503, 2007, "Real-time Stress Measurement in Ge/Si(111)-7×7 Heteroepitaxial Growth," Hideto Asaoka, et al.

In the conventional laser-beam-based methods for measuring the amount of bowing described above, only the exterior appearance of a single-crystal substrate or the exterior appearance of a single-crystal structure formed based on a single-crystal substrate is observed, but the amount of bowing itself of a crystal lattice plane of the single-crystal substrate is not measured as described above. The conventional methods therefore do not directly meet demands in the industries.

Further, in the conventional bowing measurement methods for measuring the amount of bowing of a single-crystal substrate based on how the peak position of a rocking curve changes when a position under measurement on the single-crystal substrate is changed, changing the position under measurement requires moving X-rays and the single-crystal substrate relative to each other. In the movement process, however, a target direction in which the single-crystal substrate is moved and a target distance over which the single-crystal substrate is moved often deviate from an actual movement direction and distance depending on the performance of a moving mechanism. The deviation may cause an error in bowing measurement result.

SUMMARY OF THE INVENTION

The present invention has been contrived in view of the problems described above in the conventional bowing measurement methods and apparatus. An object of the present invention is to measure the amount of bowing of a single-crystal substrate under measurement without a need to move the single-crystal substrate for reliable measurement with a small amount of error.

(Motivation of Invention)

As a single-crystal structural member used in an LED, there is a currently known single-crystal structural member having a multiple quantum well (MQW) structure in which an InGaN/GaN layer structure is formed in a deposition process on a single-crystal sapphire substrate. To evaluate the quality of the single-crystal structural member, the present inventor has performed a rocking curve measurement shown in FIG. 5. FIG. 5 shows a case where a single-crystal structural member 102 under measurement has a bowing-free, flat surface.

In general, a rocking curve relates to a technology for observing a change in the intensity of diffracted X-rays with the diffraction angle (that is, positional relationship between X-rays incident on a specimen and an X-ray detector) fixed but the incident angle of the X-rays changed with respect to the specimen. The diffraction angle is typically called "2θ." Examples of a method based on the technology include a method for swinging a specimen itself and a method for changing the position where the X-rays are incident.

In FIG. 5, X-rays R1 are incident on an X-ray irradiation area B of the single-crystal structural member 102 at an incident angle θ. The incident angle θ has been so set that GaN (0002) reflection produces diffracted X-rays R2. The incident X-rays R1 are shaped by a slit so as to have a rectangular cross-sectional shape D. The cross-sectional shape D is defined by a beam width W and a beam height H. An irradiation width L of the X-ray irradiation area B is defined as follows:

$$L=(W/\sin \theta).$$

An irradiation height H is equal to the beam height H of the incident X-rays R1. Since the beam width W is equal to the width of the slit, the beam width W is called a slit width W in some cases in the following description.

FIG. 7 shows 2θ/θ measured profiles obtained by swinging the single-crystal structural member 102 around a line X1 passing through the X-ray irradiation area B and measuring the intensity of the diffracted X-rays R2 at a plurality of swung angles different from each other. In FIG. 7, the vertical axis represents the intensity of the diffracted X-rays R2, and the horizontal axis represents the diffraction angle 2θ. A curve K1 shows a measurement result in a case where the slit width W is as wide as 1 mm, and a curve K2 shows a measurement result in a case where the slit width W is as narrow as 0.1 mm.

In FIG. 5, it was assumed that the single-crystal structural member 102 has a, bowing-free, flat surface. In practice, however, the single-crystal structural member 102 has bowing of a curvature radius R in some cases, as shown in FIG. 6. When the single-crystal structural member 102 has bowing and is irradiated with a wide X-ray flux, diffracted X-rays that exit a variety of portions of the X-ray irradiation area B travel in a variety of directions. It has been found that counting diffracted X-rays that travel in the variety of directions as a whole does not provide an accurate, detailed intensity oscillation waveform in a resultant 2θ/θ measured profile.

The fact shown in the 2θ/θ measured profiles in FIG. 7 that the oscillation waveform of the curve K1 for the wide slit width is rough, whereas the vibration waveform of the curve K2 for the narrow slit width is fine clearly shows that the diffracted X-rays travel in a variety of directions due to the bowing of the single-crystal structural member described above. To reduce the effect of the bowing of the single-crystal structural member 102 and make reliable evaluation, the present inventor has acquired correct data, for example, by minimizing the width of the incident slit or placing an analyzer crystal element, on the X-ray receiving side for the 2θ/θ measurement.

As described above, when a specimen has bowing and a wide area of a surface of the specimen is irradiated with an incident X-ray flux having a width set at a large value, the width of the rocking curve undesirably increases due to the bowing of the specimen under measurement. In view of the fact described above, the present inventor has come to believe that performing rocking curve measurement by changing the width of the X-ray flux incident on a specimen having bowing allows the peak width of the rocking curve to change and further come to think that the amount of bowing (that is, curvature radius) of the specimen can be determined based on the relationship between the peak width and the width of the incident slit.

(Experiment 1)

The present inventor used a single-crystal sapphire substrate having a radius curvature of 1 m as a specimen and changed the width of the incident slit from 0.1 to 0.8 mm at intervals of 0.1 mm to measure the width of a rocking curve for the specimen. As a result, results illustrated by the graphs shown in FIG. 8 were obtained. The resultant line K3 represents a result of measurement of sapphire (0006) reflection with an X-ray incident angle of 20° with respect to the specimen. Further, the resultant line K4 represents a result of measurement of sapphire (00012) reflection with an X-ray incident angle of 45° with respect to the specimen.

The graphs in FIG. 8 show that the rocking curve width is linearly proportional to the incident slit width. This indicates that the bowing (that is, curvature radius) of a specimen can be analyzed based on the relationship between the rocking curve width and the incident slit width. That is, it is found that the bowing of a specimen can be determined without translating the specimen but by changing the incident slit width for rocking curve acquisiLion.

Further, the graphs in FIG. 8 show that the gradient of the curve K3 for the smaller X-ray incident angle is greater than the gradient of the curve K4 for the greater X-ray incident angle. This indicates that a smaller X-ray incident angle allows an increase in evaluation sensitivity (that is, ease of evaluation) because the amount of change in the rocking curve width increases.

(Experiment 2)

The present inventor performed model calculation to determine how much the rocking curve width changes when the incident slit width is changed on the assumption that rocking curves are measured by using single-crystal sapphire substrates having a curvature radius of 1 m, 5 m, 10 m, 25 m, and 50 m as specimens. In this calculation, the following assumptions were made: Monochromatic X-rays were produced by using a Ge (220) channel-cut monochromator as an optical element and collimated before incident on the specimen; the incident angle of the X-rays incident on the surface of the sapphire substrate was about 20°; and the width of the incident slit was changed from 0.1 to 0.8 mm at intervals of 0.1 mm.

The graphs shown in FIG. 9 were obtained by plotting results of the model calculation described above. In FIG. 9, lines M1, M5, M10, M25, and M50 represent how the rocking curve width for the single-crystal sapphire substrates having a curvature radius of 1 m, 5 m, 10 m, 25 m, and 50 m changes. The graphs show that the greater the curvature radius (that is, the smaller the amount of bowing, i.e., the flatter the surface), the smaller the gradients of the lines M1 to M50, which represent the change in the rocking curve width. This means that knowledge of the gradient of the line representing the change in the rocking curve width should determine the curvature radius of an object under measurement.

(Configuration of Invention)

A first method for measuring the amount of bowing of a single-crystal substrate according to the present invention has been made based on the motive of the present invention described above and experiments and considerations associated thereto and is characterized by the following configurations: That is, the method includes setting at least two values of an X-ray irradiation width for a single specimen, measuring a rocking curve for each of the X-ray irradiation widths, determining a value of a rocking curve width for each of the rocking curves, plotting the values of the X-ray irradiation width and the values of the rocking curve width on a planar coordinate system having one axis representing the value of the rocking curve width and another axis representing the value of the X-ray irradiation width and determining a rocking curve width shift line based on the plotted points, determining a gradient of the rocking curve width shift line, and determining a curvature radius of the specimen based on the gradient.

A second method for measuring the amount of bowing of a single-crystal substrate according to the present invention includes setting at least one value of an X-ray irradiation width for a single specimen, measuring a rocking curve for the X-ray irradiation width, determining a value of a rocking curve width for the rocking curve, plotting the value of the X-ray irradiation width and the value of the rocking curve width on a planar coordinate system having one axis representing the value of the rocking curve width and another axis representing the value of the X-ray irradiation width and connecting the plotted poinL to an origin of the coordinate system or connecting the plotted point to a point in the vicinity of the origin of the coordinate system to determine a rocking curve width shift line, determining a gradient of the rocking curve width shift line, and determining a curvature radius of the specimen based on the gradient.

What is common to the first method for measuring the amount of bowing of a single-crystal substrate and the second method for measuring the amount of bowing of a single-crystal substrate is the determination of a rocking curve width shift line based on at least two plotted points. The two measuring methods differ from each other in that in the first method for measuring the amount of bowing of a single-crystal substrate, the at least two plotted points are determined by actual rocking curve measurement, whereas in the second method for measuring the amount of bowing of a single-crystal substrate, at least one of the plotted points is determined by actual rocking curve measurement and the other plotted point is determined in advance by using the origin itself of the coordinate system or a point in the vicinity of the origin.

In the first method for measuring the amount of bowing of a single-crystal substrate according to the present invention, the at least two X-ray irradiation widths may be provided by changing a width of a slit provided between an X-ray source and the specimen.

In the first method for measuring the amount of bowing of a single-crystal substrate according to the present invention, the at least two X-ray irradiation widths may be provided by changing an X-ray incident angle with respect to the specimen to cause X-rays to be diffracted at crystal lattice planes having different plane indices in the specimen.

A first apparatus for measuring the amount of bowing of a single-crystal substrate according to the present invention includes means for measuring rocking curves by changing an incident angle θ with respect to a specimen with a diffraction angle 2θ fixed, means for changing an X-ray irradiation width, means for computing a rocking curve width for each of the measured rocking curves, means for plotting the X-ray irradiation width values and the rocking curve width values on a planar coordinate system having one axis representing the rocking curve width value and another axis representing the X-ray irradiation width value and determining a rocking curve width shift line based on the plotted points, means for determining a gradient of the rocking curve width shift line, and means for determining a curvature radius of the specimen based on the gradient. The measuring apparatus is suitable to perform the first method for measuring the amount of bowing of a single-crystal substrate described above.

A second apparatus for measuring the amount of bowing of a single-crystal substrate according to the present invention includes means for measuring rocking curves by changing an incident angle θ with respect to a specimen with a diffraction angle 2θ fixed, means for computing a rocking curve width for each of the measured rocking curves, means for plotting one X-ray irradiation width value and one of the rocking curve width values on a planar coordinate system having one axis representing the rocking curve width value and another axis representing the X-ray irradiation width value and determining a rocking curve width shift line based on the plotted point and an origin of the planar coordinate system, means for determining a gradient of the rocking curve width shift line, and means for determining a curvature radius of the specimen based on the gradient. The measuring apparatus is suitable to perform the second method for measuring the amount of bowing of a single-crystal substrate described above.

In the first apparatus for measuring the amount of bowing of a single-crystal substrate according to the present invention, a slit having a variable width may be provided between an X-ray source and the specimen to provide the at least two X-ray irradiation widths.

The first apparatus for measuring the amount of bowing of a single-crystal substrate according to the present invention may further includes means for changing an X-ray incident angle with respect to the specimen to cause X-rays to be diffracted at crystal lattice planes having different plane indices in the specimen in order to provide the at least two X-ray irradiation widths.

(Merits of the Invention)

In the conventional methods for measuring the amount of bowing of a single-crystal substrate, a rocking curve is measured by translating a specimen itself to change an X-ray irradiation point instead of changing the X-ray irradiation width. That is, the measurement is made based on what is called a mapping measurement approach. In this case, when the specimen is moved, the amount of movement of the specimen may undesirably vary, resulting in a decrease in reliability of a result of measurement of the curvature radius, that is, a result of measurement of the amount of bowing.

In contrast, according to the first method and apparatus for measuring the amount of bowing of a single-crystal substrate and the second method and apparatus for measuring the amount of bowing of a single-crystal substrate according to the present invention, rocking curve measurement is performed by changing the X-ray irradiation width for a specimen, the rocking curve width is calculated based on each of the rocking curves determined in the measurement, and the curvature radius of the specimen is determined based on the rocking curve widths. As described above, in the present invention, since it is not required to move a specimen itself for the measurement, the reliability of a result of measurement of the amount of bowing is significantly improved.

Figure 1:
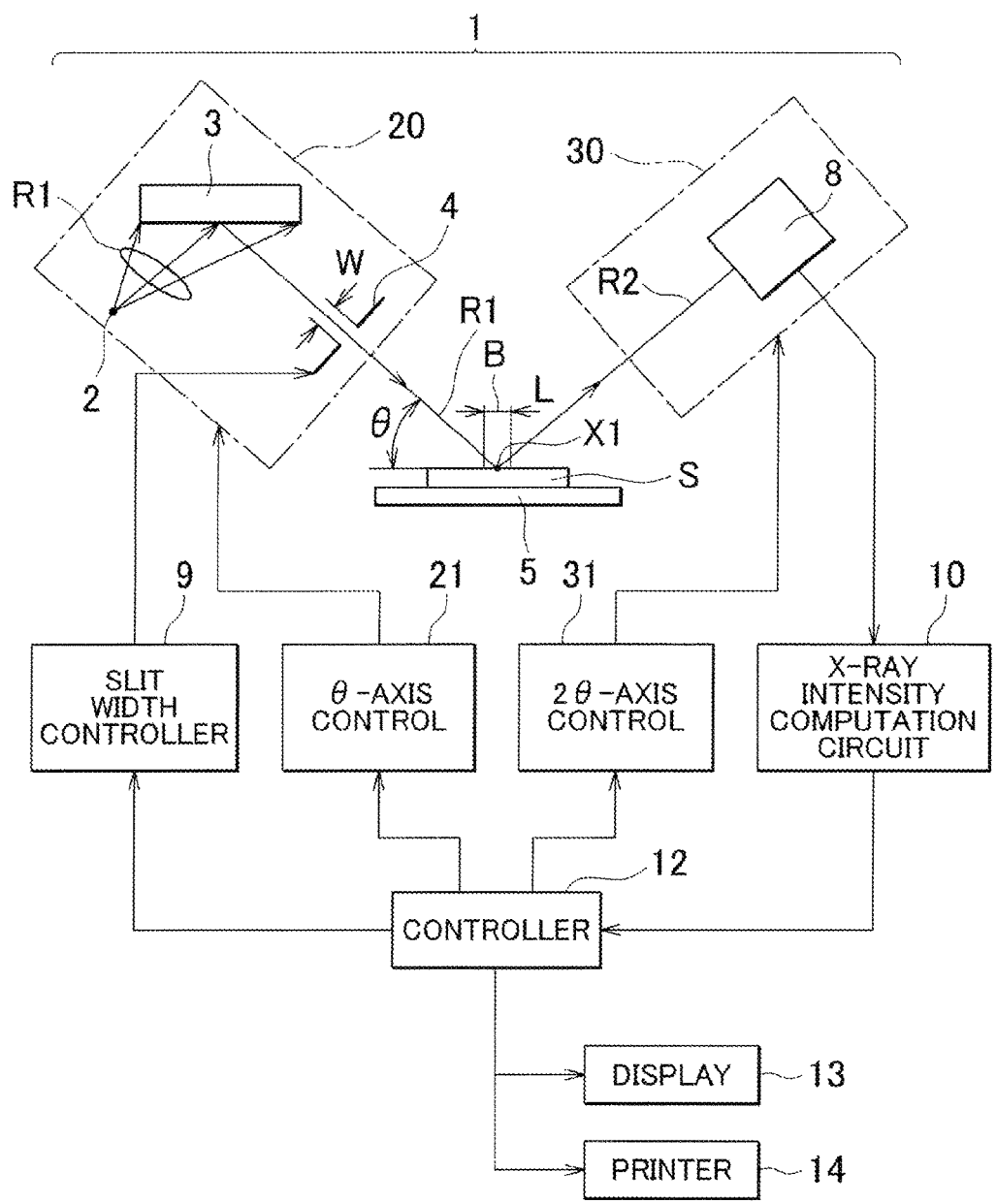
FIG. 1 shows an embodiment of an apparatus for measuring the amount of bowing of a single-crystal substrate according to the present invention.

DESCRIPTION OF THE PREFERRED EMBODIMENTS (First Embodiment of Method and Apparatus for Measuring the Amount of Bowing of a Single-Crystal Substrate)

Embodiments of a method and apparatus for measuring the amount of bowing of a single-crystal substrate according to the present invention will be described below. It is noted that the present invention is not limited to the embodiments of course, as shall be apparent. Further, in the drawings attached to the specification, each component is so drawn in some cases at a scale different from the actual scale that a characteristic portion of the component is clearly shown.

FIG. 1 shows an embodiment of an apparatus for measuring the amount of bowing of a single-crystal substrate according to the present invention. The measuring apparatus 1 includes: an incident optical system 20; a specimen support base 5, which supports a specimen S; and a reception optical system 30. The incident optical system 20 includes: an X-ray source 2, which emits X-rays; a monochromator 3, which produces monochromatic X-rays; and a slit member 4, which shapes the cross-sectional shape of the X-rays. The incident optical system 20 may further include X-ray optical elements other than those described above as required in some cases, but such other elements are not shown in FIG. 1. The receiving optical system 30 includes an X-ray detector 8, which detects x-rays emitted from the specimen S. The receiving optical system 30 may further include X-ray optical elements other than that described above as required in some cases, but such other elements are not shown in FIG. 1

The specimen S is a single-crystal substrate itself or an substance containing a single-crystal substrate. The X-ray source 2 is formed, for example, of a filament (cathode) that produces thermal electrons and a target (anti-cathode, that is, anode) on which the thermal electrons impinge. The X-ray detector 8 may be a zero-dimensional X-ray detector having no positional resolution, a one-dimensional X-ray detector having positional resolution along a straight line, or a two-dimensional X-ray detector having positional resolution in a planar area.

The slit member 4 has a structure in which an X-ray blocking member forms a slit through which X-rays are allowed to pass. The slit is an X-ray passage window that defines the beam width W and the beam height. H of X-rays shown in FIG. 5. In the present embodiment, the X-ray blocking member can be moved to adjust the slit width that defines the X-ray beam width W (reference character W also denotes slit width). The size of the X-ray irradiation width L can be adjusted by changing the slit width w of the slit member 4 to adjust the X-ray beam width W shown in FIG. 5.

The slit member 4 in FIG. 1 is accompanied by a slit width controller 9. The slit width controller 9 is a device that adjusts the size of the slit width W of the slit member 4. The slit width controller 9, which is formed of an open/close mechanism driven by a servo motor, a pulse motor, or any other drive source, can adjust the slit width by opening/closing an X-ray blocking portion of the slit member 4.

The X-ray detector 8 is accompanied by an X-ray intensity computation circuit 10. The X-ray detector 8 outputs a pulse signal corresponding to acquired X-rays. The X-ray intensity computation circuit 10 counts the pulse signal and outputs an X-ray intensity signal based on the count. The X-ray intensity signal is expressed, for example, by a count per second (cps). The X-ray intensity computation circuit 10 is incorporated in the X-ray detector 8 in some cases.

The incident optical system 20 is accompanied by a θ-axis controller 21. The θ-axis controller 21 rotates the incident optical system 20 around the center line X1, which passes through the specimen S (extends in direction perpendicular to plane of view of FIG. 1). The rotation is typically called θ-rotation. The reception optical system 30 is accompanied by a 2θ-axis controller 31. The 2θ-axis controller 31 rotates the reception optical system 30 around the center line X1. The rotation is typically called 2θ-rotation. Each of the θ-axis controller 21 and the 2θ-axis controller 31 can, for example, employ a configuration in which a power source transmits power via a power transmission mechanism to an output shaft to rotate the output shaft. The power source in this case can, for example, be a servo motor, a pulse motor, or any other motor capable of controlling the angle of rotation. Further, the power transmission mechanism can, for example, be a power transmission apparatus formed of a worm gear and a worm wheel.

The slit width controller 9, the θ-axis controller 21, the 2θ-axis controller 31, and the X-ray intensity computation circuit 10 are electrically connected to a controller 12. The controller 12 is formed, for example, of a computer and includes a central processing unit (CPU) and a memory as a storage medium. In the memory, an application program for controlling the action of the measuring apparatus 1 is installed, and storage areas for storing a variety of data are set. The controller 12 has an output port connected to a display 13 for displaying data in the form of an image, a printer 14 for printing the data, and other image display apparatus.

Figure 5:
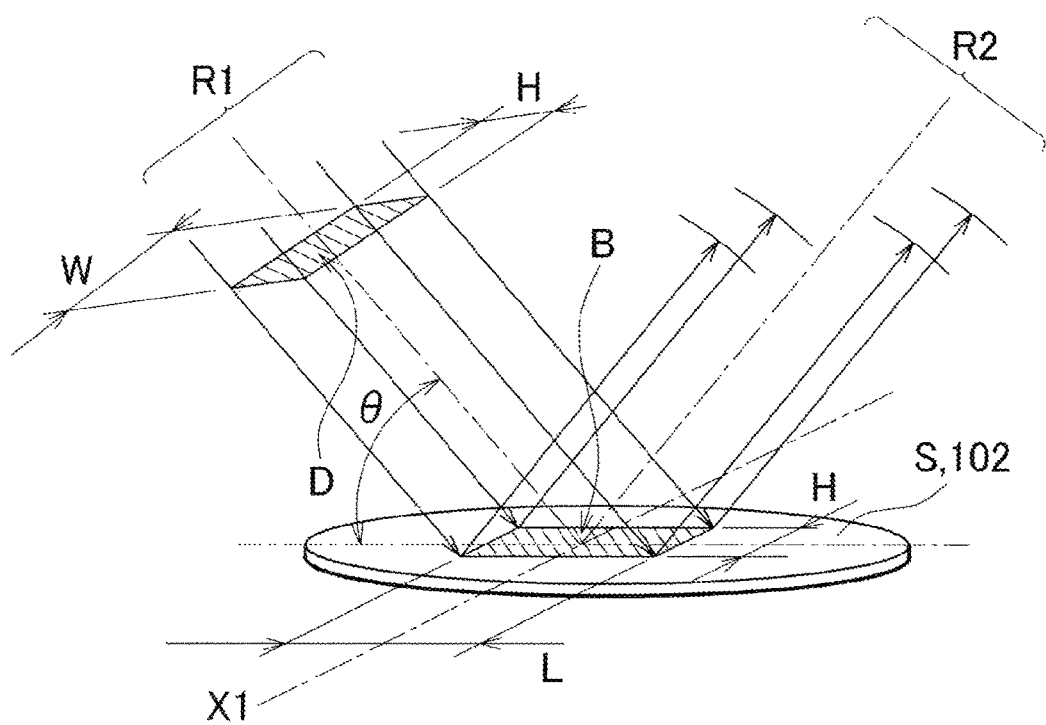
FIG. 5 diagrammatically shows how X-rays are diffracted when the measuring apparatus shown in FIG. 1 measures a flat specimen.

FIG. 5 diagrammatically shows how X-rays are diffracted when a flat specimen S is placed on the specimen base 5 in FIG. 1. The width L of the X-ray irradiation area B on the surface of the specimen S is expressed as follows:

$$L = W/\sin\theta \tag{1}$$

W: X-ray beam width (that is, slit width of slit 4)
θ: X-ray incident angle

Figure 6:
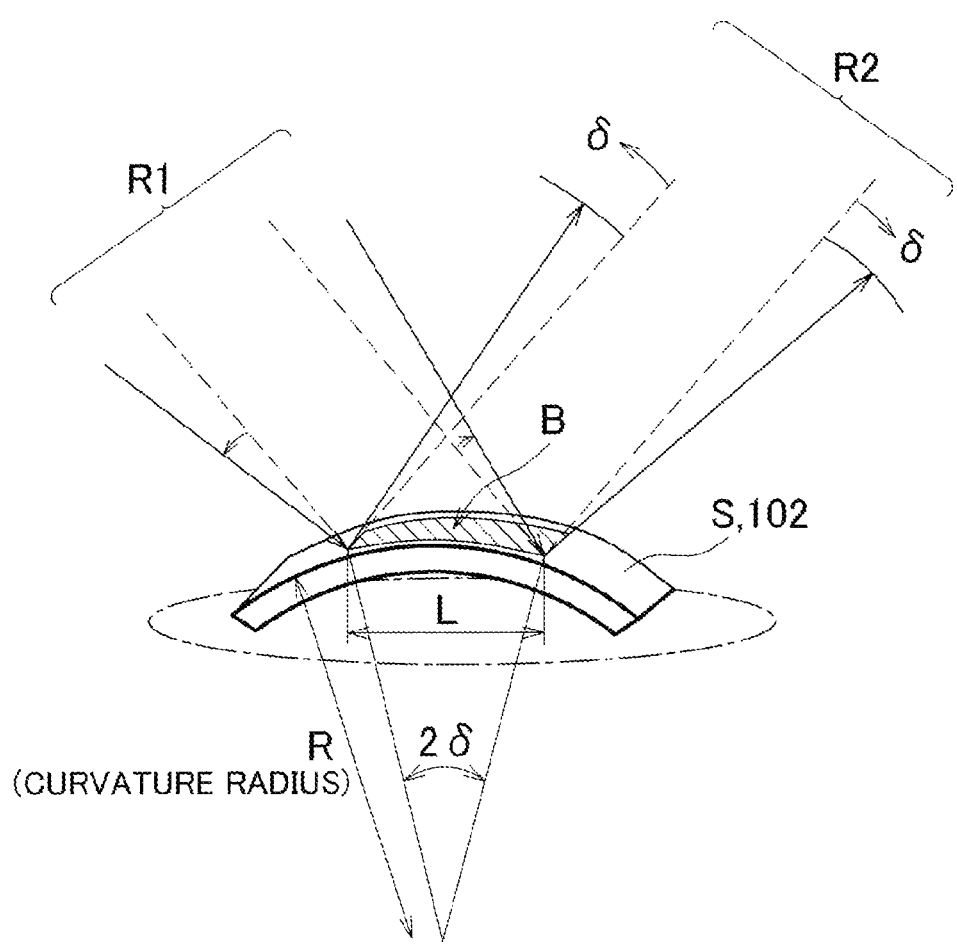
FIG. 6 diagrammatically shows how X-rays are diffracted when the measuring apparatus shown in FIG. 1 measures a specimen having bowing.
Figure 7:
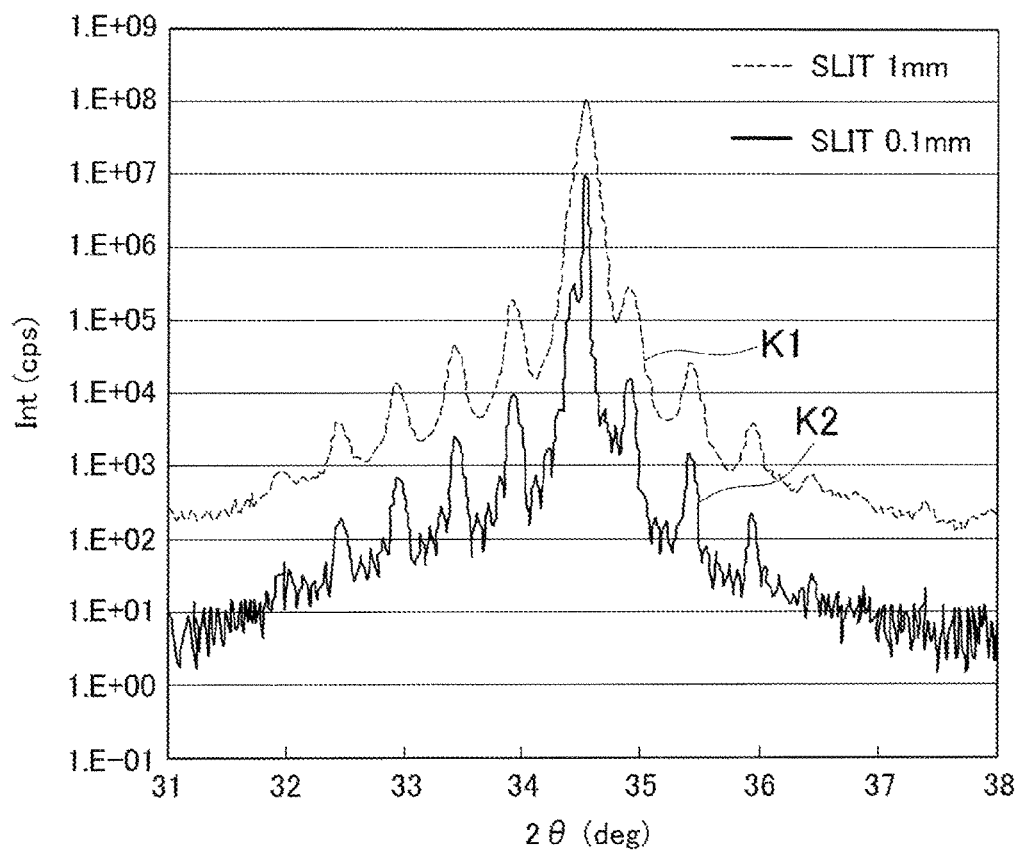
FIG. 7 shows graphs illustrating exemplary rocking curves obtained as experimental results.
Figure 8:
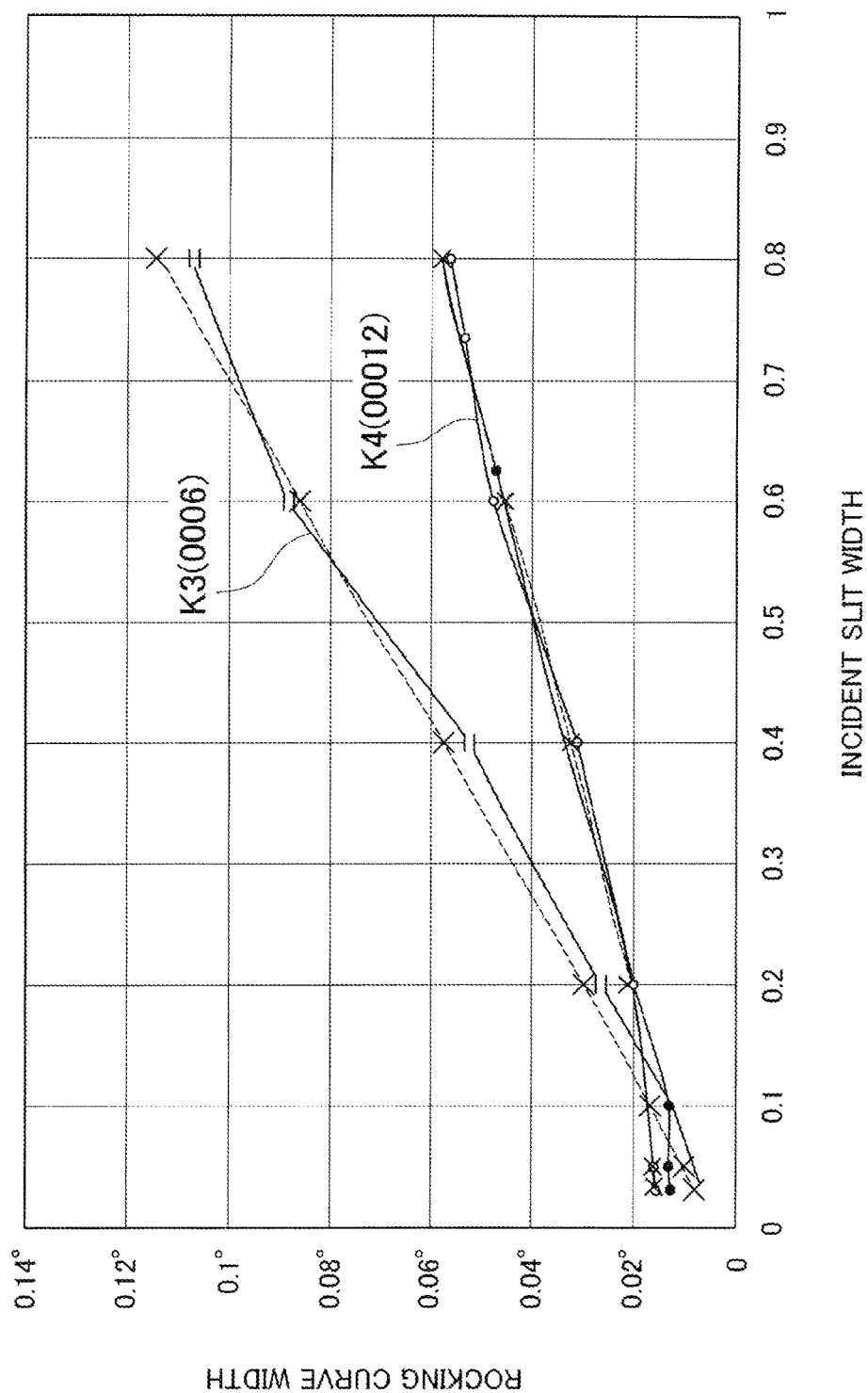
FIG. 8 shows graphs illustrating an exemplary rocking curve analysis result.
Figure 9:
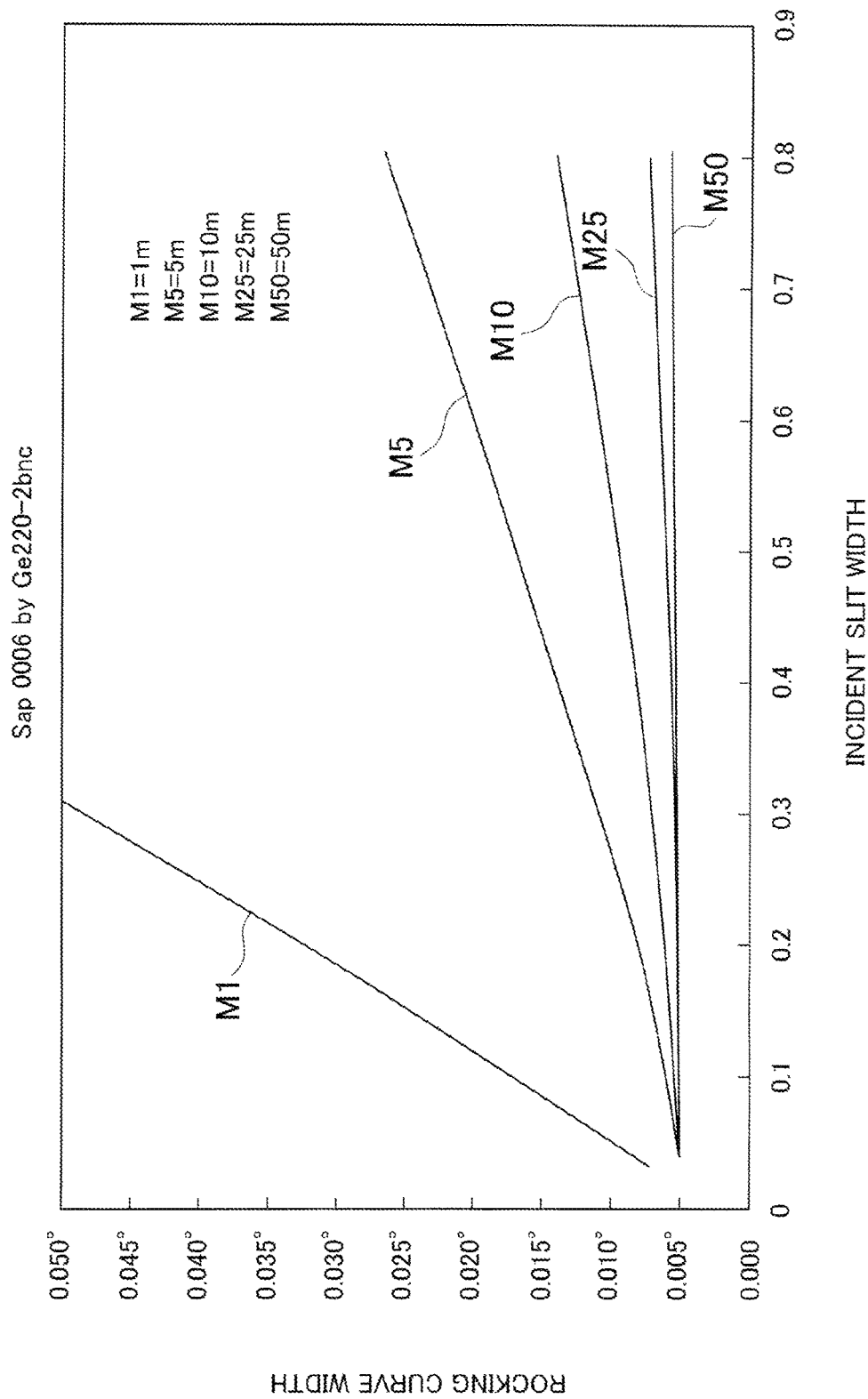
FIG. 9 shows graphs illustrating another exemplary rocking curve analysis result.

FIG. 6 diagrammatically shows how X-rays are diffracted when a bowed specimen S is placed on the specimen base 5. In FIG. 6, the specimen S has bowing of curvature radius R. When the specimen S is irradiated with X-rays in different positions, the bowing of the specimen S causes diffracted X-rays corresponding to the X-rays to travel in different directions.

It is now assumed that X-rays are incident on an area having the irradiation width L, and that the rocking curve resulting from the bowing has a divergent angle (the full width at half maximum intensity/FWHM) 2δ. Since 2δ is equal to a central angle corresponding to the irradiation width L around the center of curvature of the specimen S (labeled with reference character "2δ" in FIG. 6), the following expression is derived from the geometric relationship shown in FIG. 6:

$$\sin(2\delta/2)=(L/2)/R=(\tfrac{1}{2}R)L \qquad (2)$$

Expression (2) described above is drawn as a straight line having a gradient (½R) in a planar coordinate system having a vertical axis representing sin(2δ/2) and a horizontal axis representing L. In the coordinate system, sin(2δ/2) along the vertical axis may be replaced with the peak width itself of a rocking curve (also referred to as rocking curve width), and the curvature radius R can be calculated from the gradient of a straight line drawn in the modified coordinate system.

(Measurement of Flat Specimen S)

A description will be made of measurement performed by the measuring apparatus 1 shown in FIG. 1. First, consider a case where a flat, bowing-free specimen S is placed on the specimen base 5. The controller 12 first executes step S1 in FIG. 2. That is, the X-ray beam width W in FIG. 5 (that is, slit width W in FIG. 1) is so adjusted that the irradiation width L of the X-ray irradiation area B is set at a certain value L1. The X-ray incident angle θ is then set at a value that causes diffracted X-rays to be produced in a specific lattice plane in the specimen S.

Figure 3A:
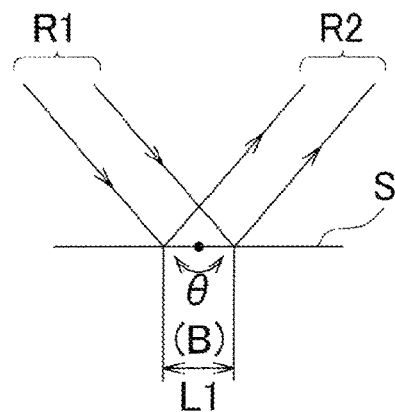
FIGS. 3A to 3E diagrammatically show the steps in FIG. 2 in a case where a flat single-crystal substrate is used as a specimen.

The X-ray source 2 in FIG. 1 is then driven to emit the X-rays R1. The X-rays R1 enter the monochromator 3, where monochromatic X-rays are produced. The slit of the slit member 4 shapes the X-rays to have a predetermined cross-sectional shape as shown in FIG. 5, and the resultant X-rays are incident on the specimen S. The area on which the X-rays are incident is the X-ray irradiation area B. When the X-ray irradiation area B is irradiated with the X-rays at the X-ray incident angle θ, which is an angle that causes diffracted X-rays to be produced, diffracted X-rays R2 are produced as shown in FIG. 3A, and the X-rays are detected with the X-ray detector 8 in FIG. 1.

The controller 12 in FIG. 1 then actuates the θ-axis controller 21, with the specimen base 5 and the X-ray detector 8 fixed, to swing the incident optical system 20 (hence incident X-rays R1) around the center line X1 within a predetermined swing range. During the swing, motion, the X-ray detector 8 detects the diffracted X-rays to provide a rocking curve RC1, such as that shown in FIG. 3B. The controller 12 further determines a rocking curve width (the full width at half maximum intensity/FWHM, for example) WR1.

Figure 3B:
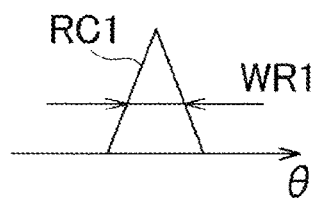
Figure 3C:
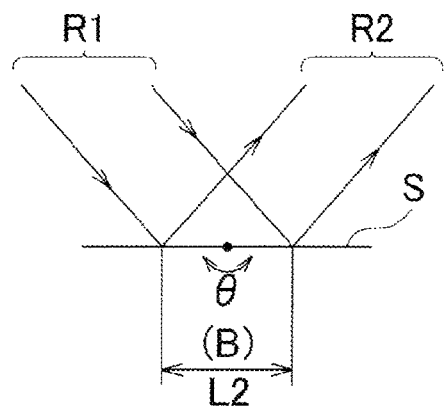
Figure 3D:
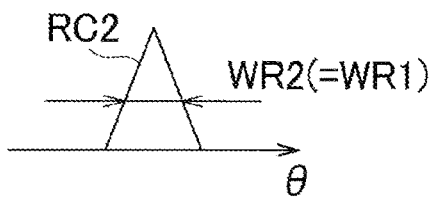

The controller 12 then actuates the slit width controller 9 to change the slit width W of the slit member 4 and hence set the X-ray irradiation width L at a value L2, which differs from the previous value L1 (FIG. 3C). In this state, a rocking curve RC2 is determined (FIG. 3D), and a rocking curve width WR2 is further determined (FIG. 3D). Since the specimen S currently under measurement is a flat specimen, the rocking curve width does not change when the X-ray irradiation width L changes. That is, WR2=WR1.

In FIGS. 3B and 3D, the rocking curve widths WR1 and WR2 show that they have a finite non-zero value even when the specimen S is a bowing-free single-crystal specimen. The finite width is a combination of a spread resulting from the optical system itself (resolution) and a spread resulting from crystallizability of the specimen itself. The spread resulting from the optical system itself (resolution) and the spread resulting from crystallizability of the specimen itself can be calculated. This means that even when a rocking curve for a specimen having actual bowing is measured, the spreads resulting from the factors described above can be calculated in advance, and the values calculated in advance can be subtracted from a measured value, whereby spread purely resulting from the bowing can be calculated. Further, when a specimen having bowing is measured, the rocking curve width for an irradiation width L of virtually zero, that is, L1=0 can be approximately calculated.

Figure 2:
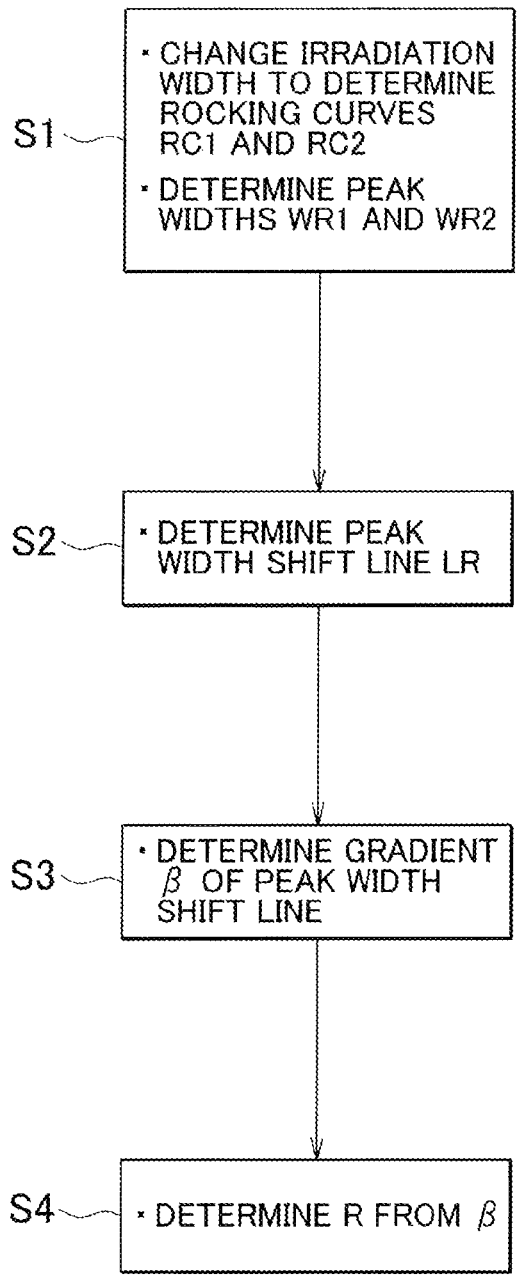
FIG. 2 is a flowchart showing part of steps executed by the measuring apparatus shown in FIG. 1.
Figure 2:
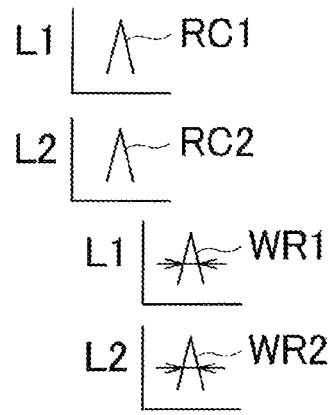
Figure 2:
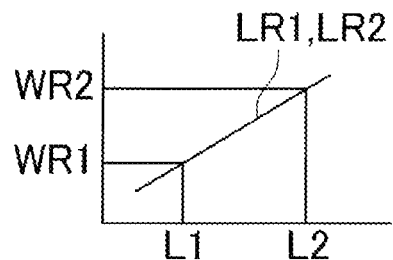
Figure 2:
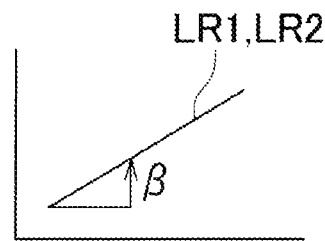
Figure 3E:
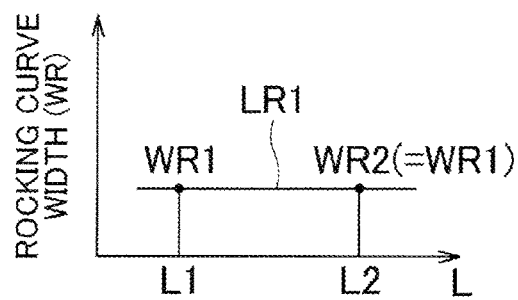

The controller 12 then determines a rocking curve width shift line in step S2 in FIG. 2. Specifically, (L1, WR1) and (L2, WR2) described above are plotted on a coordinate system having a vertical axis representing the rocking curve width WR and a horizontal axis representing the X-ray irradiation width L as shown in FIG. 3E, and the plotted points are connected to each other to form a straight line. A rocking curve width shift line LR1 is thus determined. Further, the controller 12 then determines the gradient p of the rocking curve width shift line LR1 in step S3 in FIG. 2.

As stated in the above description of Expression (2), the rocking curve width WR along the vertical axis is equivalent to the value of sin(2δ/2) in the left side of Expression (2). The gradient of the rocking curve width shift line LR1 determined in FIG. 3E is therefore equal to the gradient (½R) in Expression (2) described above. That is, the following expression is satisfied:

$$\beta=(\tfrac{1}{2}R) \qquad (3)$$

Subsequently, in step S4 in FIG. 2, the controller 12 in FIG. 1 calculates R (curvature radius) based on the gradient β determined in step S3 and Expression (3) described above. Since the flat specimen S is currently considered, and the rocking curve width WR1 for the irradiation width L1 is equal to the rocking curve width WR2 for the irradiation width L2, the gradient β of the rocking curve width shift line LR1 is therefore zero, whereby the curvature radius R is determined to be infinity (that is, the specimen S is flat).

(Measurement of Specimen S having Bowing)

Figure 4A:
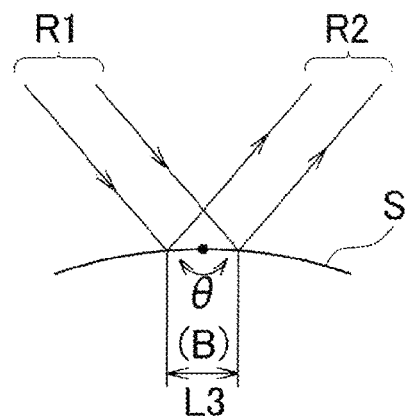
FIGS. 4A to 4E diagrammatically show the steps in FIG. 2 in a case where a single-crystal substrate having bowing is used as a specimen.
Figure 4B:
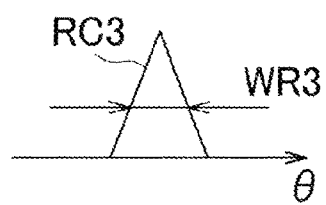
Figure 4C:
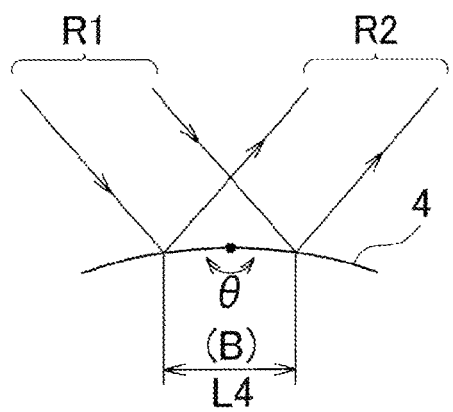
Figure 4D:
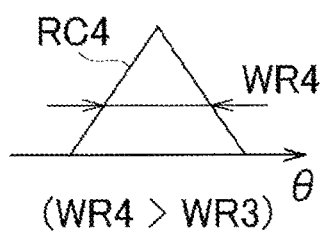

Consider next a case where a specimen S having bowing is placed on the specimen base 5 in FIG. 1. In this case as well, in step S1 in FIG. 2, X-ray irradiation areas B having irradiation widths L3 and L4 different from each other are irradiated with X-rays (FIGS. 4A and 4C). Rocking curves RC3 and RC4 for the irradiation widths L3 and L4 are measured (FIGS. 4B and 4D), and rocking curve widths WR3 and WR4 are further determined (FIGS. 4B and 4D).

Figure 4E:
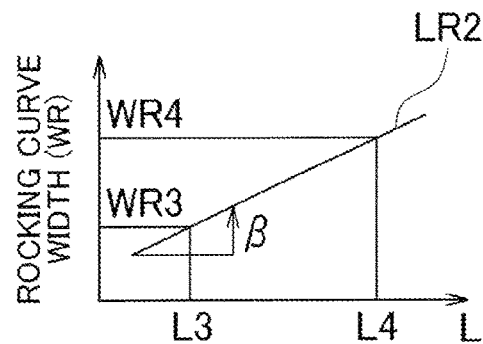

Subsequently, in step S2 in FIG. 2, a rocking curve width shift line LR2 is determined based on the X-ray irradiation widths L3 and L4 and the rocking curve widths WR3 and WR4 corresponding thereto, as shown in FIG. 4E. Further, in step S3 in FIG. 2, the gradient 1 of the rocking curve width shift line LR2 is calculated. Moreover, in step S4, the curvature radius R is calculated based on Expression (3) described above.

In the current measurement, since the specimen S has bowing and WR3≠WR4, in particular, WR3<WR4 due to the effect of the bowing, the determined curvature radius R reflects the amount of bowing of the specimen S.

In the conventional methods for measuring the amount of bowing of a single-crystal substrate, a rocking curve is measured by translating a specimen itself to change an X-ray irradiation point instead of changing the X-ray irradiation width. That is, the measurement is made based on what is called a mapping measurement approach. In this case, when the specimen is moved, the amount of movement of the specimen may undesirably vary, resulting in a decrease in reliability of a result of measurement of the curvature radius, that is, a result of measurement of the amount of bowing.

In contrast, according to the present invention, rocking curve measurement is performed by adjusting the slit width W in FIG. 1 to change the X-ray irradiation width L for the specimen S (see FIGS. 3A, 3C, 4A, and 4C); the rocking curve width is calculated based on each of the rocking curves determined in the measurement (see FIGS. 3B, 3D, 4B, and 4D); and the curvature radius R of the specimen S is determined based on the rocking curve widths (step S4 in FIG. 2). As described above, in the present embodiment, since it is not required to move a specimen itself for the measurement, the reliability of a result of measurement of the amount of bowing is significantly improved.

(Second Embodiment of Method and Apparatus for Measuring the Amount of Bowing of a Single-Crystal Substrate)

Figure 10:
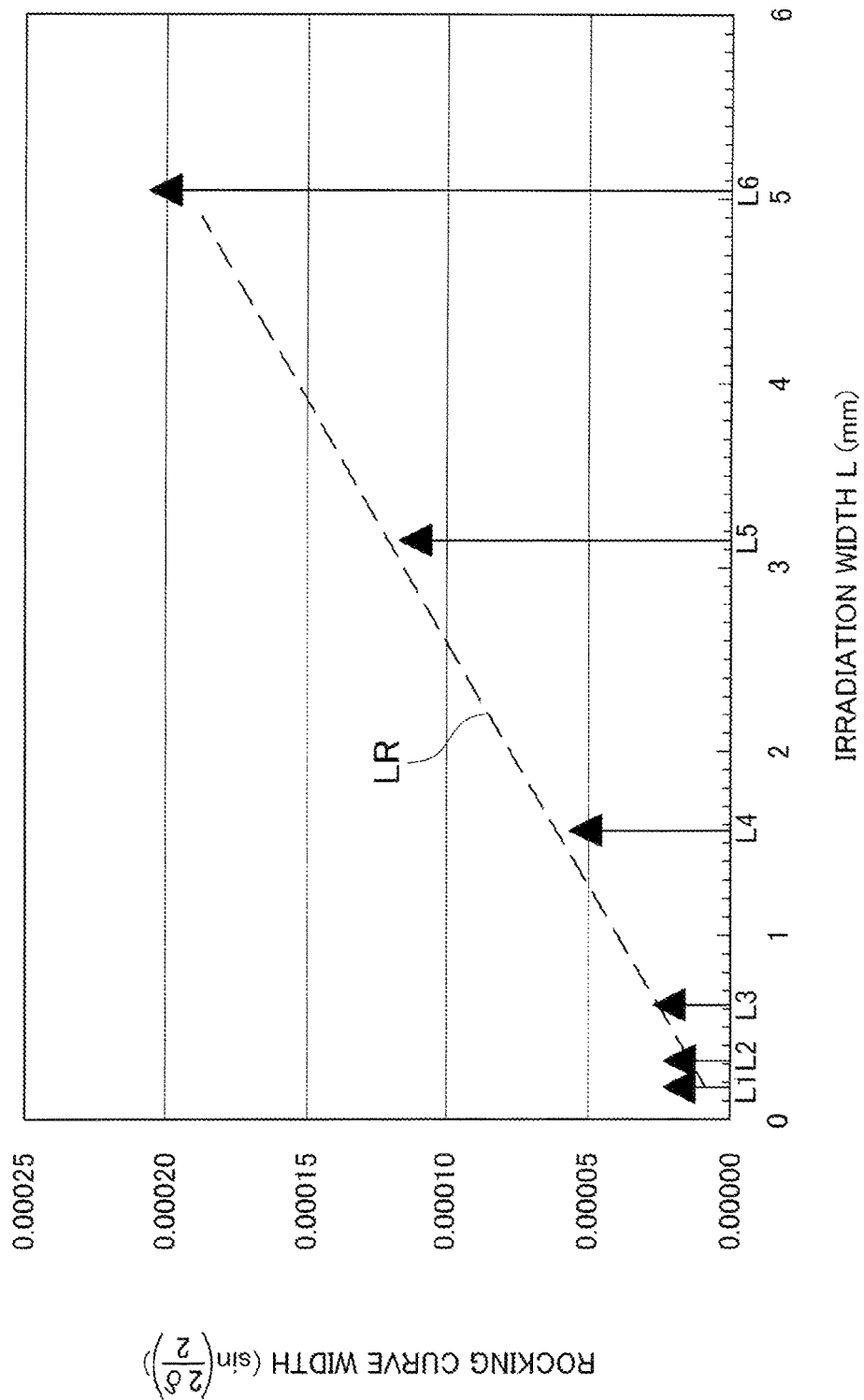
FIG. 10 shows a graph illustrating still another exemplary rocking curve analysis result.
Figure 11A:
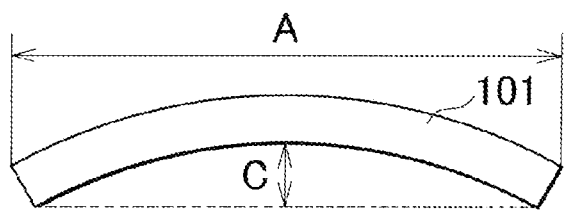
FIGS. 11A to 11C show the relationship between the amount of bowing and the curvature radius of a single-crystal substrate in the form of a figure and graphs.
Figure 11B:
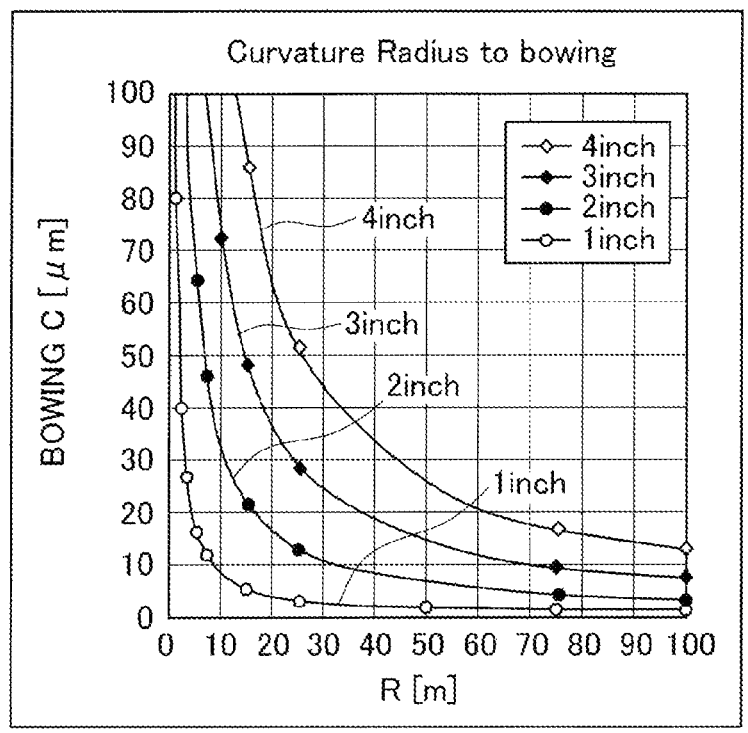
Figure 11C:
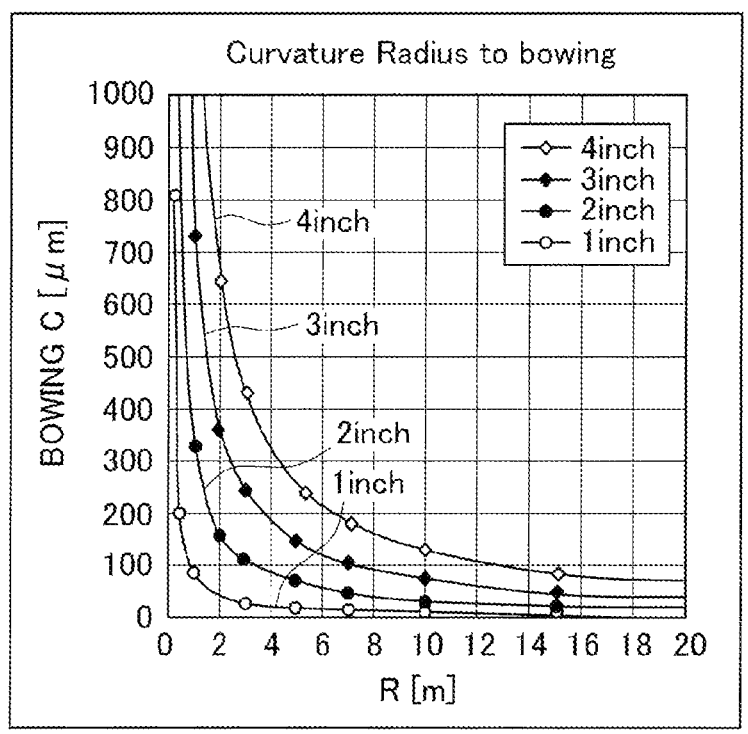

In the embodiment described above, the slit width W is changed to adjust the size of the X-ray irradiation width L on the specimen S in FIG. 1. The configuration described above can be replaced with the following configuration: That is, two or more plane indices are determined for the specimen 5, and a plurality of X-ray incident angles θ1, θ2, . . . that cause diffracted X-rays to be produced under the condition of the plane indices are determined. A rocking curve is measured for each of the X-ray incident angles θ1, θ2, . . . to determine a rocking curve width shift line LR, such as that shown in FIG. 10, and the curvature radius of the specimen (that is, the amount of bowing of the specimen) can be determined based on the rocking curve width shift line LR. In this case, the X-ray irradiation width L on the specimen S is set at a different value whenever the X-ray incident angle is changed to θ1, θ2, . . . . According to the present embodiment, variation in the measurement can be further suppressed because the slit width W is not required to be changed by using a mechanical mechanism.

EXAMPLE 1

A single-crystal structural member in which a GaN film was placed on a single-crystal sapphire substrate was used as a specimen. The following six types of X-ray irradiation width L (see FIG. 5) were set on the specimen: 0.18 mm; 0.31 mm; 0.63 mm; 1.58 mm; 3.14 mm; and 5.02 mm. In FIG. 1, the X-ray irradiation width L was changed in accordance with the six types described above to measure a rocking curve for each of the irradiation widths L. A rocking curve width was then determined for each of the irradiation widths L, and the determined rocking curve widths were plotted on the coordinate system in FIG. 10. The plotted points were processed in linear approximation to determine a rocking curve width shift line LR.

The gradient of the rocking curve width shift line LR was calculated, and the resultant gradient was 0.000038. The values of the rocking curve widths along the vertical axis were plotted after they were corrected in consideration of a spread resulting from the optical system. The gradient of the rocking curve width shift line LR was substituted into Expression (3) described above, and the curvature radius R was calculated to 13 m. That is, the calculation shows that the bowing of the specimen has the curvature radius of 13 m.

EXAMPLE 2

A single-crystal structural member in which a GaN film was placed on a single-crystal sapphire substrate was used as a specimen. In FIG. 1, the X-ray irradiation width L was set at a single value of 5.02 mm for the rocking curve measurement to determine a rocking curve width, which was plotted on the coordinate system in FIG. 10. The plotted point was connected to the origin (0, 0.00000) in the graph in FIG. 10 to determine a rocking curve width shift line LR. The rocking curve width shift line LR was a straight line substantially the same as the rocking curve width shift line LR produced in Example 1. That is, the lower left point of a rocking curve width shift line LR can be the origin of the coordinate system. It is therefore found that an appropriate single X-ray irradiation width L suffices for the rocking curve measurement.

EXAMPLE 3

A single-crystal structural member in which a GaN film was placed on a single-crystal sapphire substrate was used as a specimen. In FIG. 1, the X-ray irradiation width L was set at a single value of 5.02 mm for the rocking curve measurement to determine a rocking curve width, which was plotted on the coordinate system in FIG. 10. The plotted point was connected to an appropriate point in the vicinity of the origin (0, 0.00000) of FIG. 10 to determine a rocking curve width shift line LR. The rocking curve width shift line LR was a straight line having a gradient slightly different from that of the rocking curve width shift line LR produced in Example 1. It is, however, found that the curvature radius of the specimen can be determined with sufficient accuracy by using the rocking curve width shift line LR produced in Example 3. That is, it is found that the lower left point of a rocking curve width shift line LR can be a point in the vicinity of the origin of the coordinate system but separate therefrom by a value within an acceptable range.

(Other Embodiments)

The present invention has been described with reference to preferable embodiments, but the present invention is not limited thereto, and a variety of changes can be made to the embodiments to the extent that the changes fall within the scope of the claims.

For example, in the embodiment shown in FIG. 1, the present invention is applied to a measuring apparatus having a structure in which a rocking curve is determined by changing the position of the incident optical system 20. The present invention is, however, also applicable to a measuring apparatus having a structure in which the incident optical system 20 is fixed and the specimen support base 5 is swung around the center line X1, whereby the rocking curve is found.

DESCRIPTION OF SYMBOLS

1: Apparatus for measuring the amount of bowing of single-crystal substrate, 2: X-ray source, 3: Monochromator, 4: Slit member, 5: Specimen support base, 8: X-ray detector, 101: Single-crystal substrate, 102: Single-crystal structural member, 8: Amount of displacement, θ: X-ray incident angle, A: Measurement area, B: X-ray irradiation area, C: Bowing, D: Cross-sectional shape of incident X-rays, H: X-ray beam height, L: X-ray irradiation width, LR, LR1, LR2: Rocking cure width shift line, R: Curvature radius, R1: Incident X-rays, R2: Diffracted X-rays, RC, RC1, RC2, RC3, RC4: Rocking curve, S: Specimen, W: X-ray beam width/slit width, WR1, WR2, WR3, WR4: Rocking curve width, X1: Center line of swing motion

What is claimed is:

1. A method for measuring the amount of bowing of a single-crystal substrate, the method comprising:

setting, by a controller of a measuring apparatus, at least two values of an X-ray irradiation width for a single specimen;

emitting, by an X-ray source of the measuring apparatus, X-rays, wherein the emitted X-rays are incident on the single specimen;

detecting, by an X-ray detector of the measuring apparatus, diffracted X-rays;

measuring, by the controller of the measuring apparatus, a rocking curve, provided by the diffracted X-rays, for each of the X-ray irradiation widths;

determining, by the controller of the measuring apparatus, a value of a rocking curve width for each of the rocking curves;

plotting, by the controller of the measuring apparatus, the values of the X-ray irradiation width and the values of the rocking curve width on a planar coordinate system having one axis representing the value of the rocking curve width and another axis representing the value of the X-ray irradiation width and determining a rocking curve width shift line based on the plotted points;

determining, by the controller of the measuring apparatus, a gradient of the rocking curve width shift line; and determining, by the controller of the measuring apparatus, a curvature radius of the specimen based on the gradient, wherein the at least two X-ray irradiation widths are set by adjusting an X-ray incident angle ($\theta$) with respect to the specimen causing X-rays to be diffracted at crystal lattice planes having different plane indices in the specimen.

* * * * *